(12) United States Patent
Wilson et al.

(10) Patent No.: US 6,313,360 B1
(45) Date of Patent: Nov. 6, 2001

(54) PROCESS FOR THE MANUFACTURE OF 1, 1, 1, 3, 3-PENTACHLOROPROPANE

(75) Inventors: Richard Wilson, Mulvane; Rodney Klausmeyer; Lloyd Branam, both of Wichita; Derrek Burrows; Jim Strathe, both of Wichita; John Dawkins, Derby, all of KS (US); Theo Lichtenstein, Miami, FL (US); Joseph Weller, Mulvane; John Tummons, Wichita, both of KS (US)

(73) Assignee: Vulcan Materials Company, Birmingham, AL (US)

( * ) Notice: Subject to any disclaimer, the term of this patent is extended or adjusted under 35 U.S.C. 154(b) by 0 days.

(21) Appl. No.: 09/671,993

(22) Filed: Sep. 29, 2000

(51) Int. Cl.$^7$ .................................................. C07C 17/26
(52) U.S. Cl. ............................................... 570/257
(58) Field of Search .............................. 570/257

(56) References Cited

U.S. PATENT DOCUMENTS 6,187,978 * 2/2001 Rygas et al. ....................... 570/257

FOREIGN PATENT DOCUMENTS

WO 00/68172    11/2000   (WO) .

* cited by examiner

Primary Examiner—Alan Siegel
(74) Attorney, Agent, or Firm—Bradley Arant Rose & White, LLP

(57) ABSTRACT

A process is provided for the production of 1,1,1,3,3-pentachloropropane. The process comprises: (a) producing a product mixture in a reactor by reacting carbon tetrachloride and vinyl chloride in the presence of a catalyst mixture comprising organophosphate solvent, iron metal and ferric chloride under conditions sufficient to produce 1,1,1,3,3-pentachloropropane; (b) subjecting the 1,1,1,3,3-pentachloropropane containing product mixture from step (a) to evaporation such that a fraction enriched in 1,1,1,3,3-pentachloropropane is separated from the product mixture and a bottoms fraction results which comprises the iron metal/ferric chloride catalyst components and heavy end by-products; and (c) recycling at least a portion of the bottoms fraction from step (b) to the reactor.

8 Claims, 1 Drawing Sheet

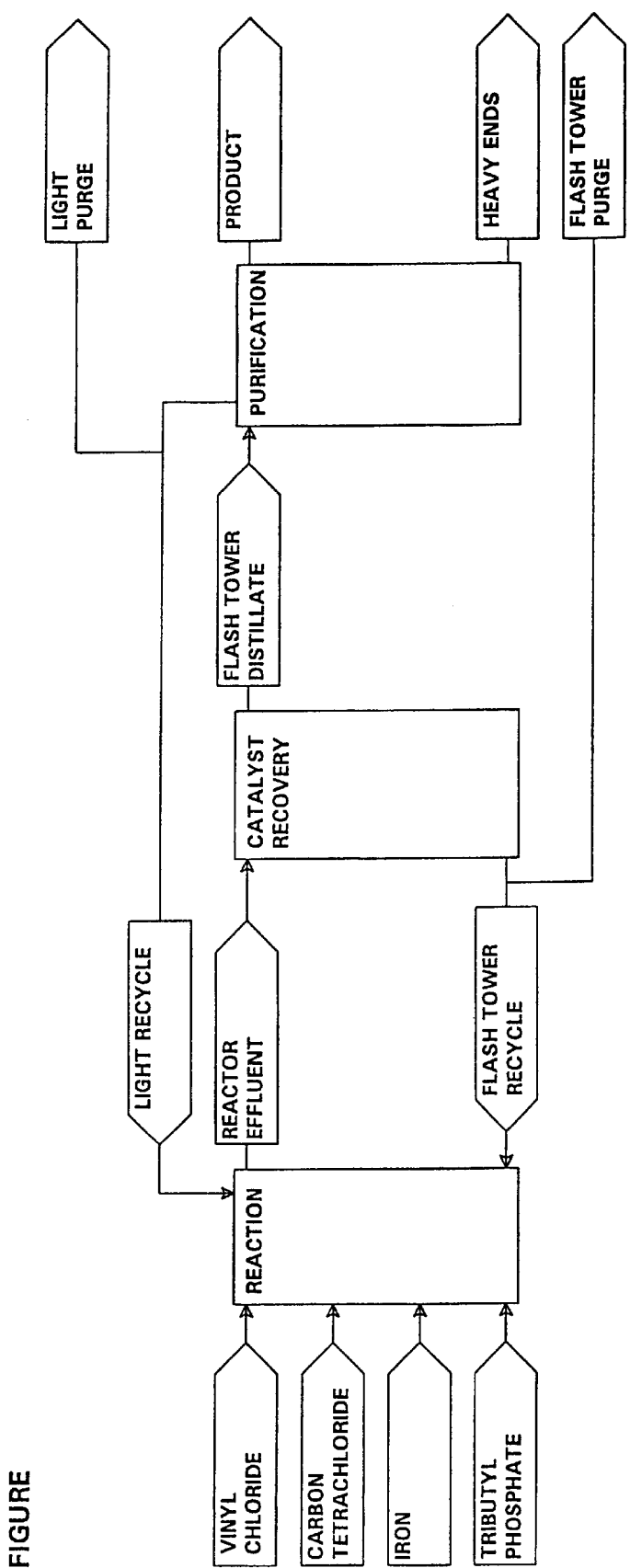
FIGURE

PROCESS FOR THE MANUFACTURE OF 1, 1, 1, 3, 3-PENTACHLOROPROPANE

BACKGROUND OF THE INVENTION

1. Field of the Invention

The present invention relates to a process for the manufacture of 1,1,1,3,3-pentachloropropane.

2. Description of the Related Art

The Montreal Protocol of 1987 placed a ban on certain substances that deplete the ozone layer, especially chlorofluorocarbons (CFC's). To hasten the elimination of CFC production and use, the Protocol allowed for certain fluorocarbon products (HCFC's) to be used as "bridge replacements." Although these bridge replacements are considerably more ozone friendly than CFC'S, they are intended to be transitional and not permanent replacements. Fluorocarbon producers are actively pursuing replacement HFC candidates known as "third generation fluorocarbons." These third generation fluorocarbons will require hydrochlorocarbon feedstocks.

The second largest U.S. fluorochemical end-use market, next to refrigeration, is for blowing agents utilized in the manufacture various synthetic plastic formed products. CFC-11 was the dominant product in this market, however, it has been replaced by the bridge-fluorocarbon HCFC-141b. Because, by regulation, foam manufacturers must switch away from HCFC-141b by the year 2003, new third generation fluorocarbon products must be developed and commercialized.

Several fluorochemical producers have targeted fluorocarbon 1,1,1,3,3-pentafluoropropane, utilizing 1,1,1,3,3-pentachloropropane as the hydrochlorocarbon feedstock, as the primary replacement product for foam blowing applications. Zil'bennan et al. ("Synthesis of liquid telomers of vinyl chloride with carbon tetrachloride", *J. Org. Chem.* USSR (English Transl.), 3:2101–2105, 1967) prepared 1,1,1,3,3-penta-chloropropane in a 58% yield by the reaction of carbon tetrachloride ($CCl_4$) and vinyl chloride using ferrous chloride tetrahydrate in isopropanol. In addition, Kotora et.al. ("Addition of tetrachloromethane to halogenated ethenes catalyzed by transition metal complexes", *J. Mol. Catal.*, 77(1):51–60, 1992) prepared 1,1,1,3,3-pentachloropropane in high yields using either cuprous chloride/butylamine or tris(triphenylphosphine) dichlororuthenium.

European Patent Application No. 131561 describes a very general process for the addition of a haloalkane compound to an alkene or alkyne compound in the presence of iron metal and a phosphorus (V) compound, to form halogenated alkanes. EP 131561 sets forth several examples of the batch reaction of ethylene and carbon tetrachloride to produce 1,1,1,3-tetrachloropropane. EP 131561 also mentions a wide variety of other olefins and alkynes, including vinyl halides. It states that the batch process could be made continuous, but does not include any specifics on how this would be carried out.

Despite the known processes, improvements are needed in the manufacture of 1,1,1,3,3 -pentachloropropane. The present invention is directed to such an improved process.

OBJECTS AND SUMMARY OF THE INVENTION

It is an object of the present invention to provide an improved process for the production of 1,1,1,3,3-pentachloropropane. The process preferably enhances throughput, extends catalyst life, and maximizes feedstock conversion.

In one aspect, the invention provides a continuous process for the production of 1,1,1,3,3-pentachloropropane, including:

a) producing a product mixture in a reactor by reacting carbon tetrachloride and vinyl chloride in the presence of a catalyst mixture comprising organophosphate solvent, iron metal and ferric chloride under conditions sufficient to produce 1,1,1,3,3-pentachloropropane;

b) subjecting the 1,1,1,3,3-pentachloropropane-containing product mixture from step (a) to evaporation such that a fraction enriched in 1,1,1,3,3-pentachloropropane is separated from the product mixture and a bottoms fraction results which includes the iron metal/ferric chloride catalyst components and heavy end by-products; and c) recycling at least a portion of the bottoms fraction from step (b) to the reactor.

In accordance with another aspect of the invention a system for manufacturing 1,1,1,3,3-pentachloropropane is provided. The system includes:

a) a reactor wherein carbon tetrachloride and vinyl chloride in the presence of a catalyst mixture including organophosphate solvent, iron metal and ferric chloride are reacted under conditions sufficient to produce 1,1,1,3,3-pentachloropropane effluent;

b) a catalyst recovery device, wherein the 1,1,1,3,3-pentachloropropane reactor effluent is received and distilled such that a fraction enriched in 1,1,1,3,3-pentachloropropane is separated from a bottoms fraction including organophosphate/ferric chloride catalyst components and heavy end by-products; and c) a conduit to convey at least a portion of the bottoms fraction from step (b) to the reactor.

BRIEF DESCRIPTION OF THE DRAWING

The objects and advantages of the invention will become apparent from the following detailed description of the preferred embodiments thereof in connection with the accompanying drawing, in which:

The FIGURE of the drawing is a schematic diagram of a novel process for the production of 1,1,1,3,3,-pentachloropropane.

DETAILED DESCRIPTION OF THE PREFERRED EMBODIMENTS OF THE INVENTION

The present invention relates to a process for the manufacture of hydrochlorocarbon. This process uses a catalyst mixture to manufacture 1,1,1,3,3-pentachloropropane from carbon tetrachloride and vinyl chloride. Tributyl phosphate (TBP), metallic iron, ferrous chloride, and ferric chloride are components of the catalyst mixture—hereafter referred to as catalyst. The catalyst promotes the following Kharasch reaction: $CCl_4 + CH_2=CHCl \rightarrow CHCl_2-CH_2-CCl_3$ (1,1,1,3,3-pentachloropropane)

The 1,1,1,3,3-pentachloropropane process includes three steps as shown in the figure: reaction, catalyst recovery, and purification.

Reaction Step

In accordance with a preferred embodiment, vinyl chloride, carbon tetrachloride, tributyl phosphate (TBP), and iron are continually fed into a reactor. Vinyl chloride may be fed as a liquid or vapor, but liquid vinyl chloride is preferred.

Metallic iron in any form may be used, but powder is preferred. Metallic iron may be added to the reactor by any means, but powder slurry in carbon tetrachloride is preferred. Light recycle and flash tower recycle are reactor feeds as described below.

The reactor is an agitated vessel made of corrosion resistant materials in process wetted areas. Nickel alloys, PTFE, tantalum, and glass-lined steel are preferred process wetted materials. Examples include nickel alloys such as Nickel 200, Hastelloy™ C-276, and Monel™. The reactor is capable of removing reaction heat through a number of devices. For example, reaction heat may be removed by circulating reactor contents through an external heat exchanger, by internal coils, or an external cooling jacket. External coils or a baffled external jacket are preferred for simplicity and low potential for leakage.

The reactor is agitated to mix reactor feeds and keep iron powder suspended. Powdered iron is consumed in the reactor, making ferrous chloride and ferric chloride. These components, (i.e., ferrous chloride and ferric chloride), and TBP form complexes miscible in reactor contents. These complexes are catalytic and promote the Kharasch reaction. Side reactions produce chlorinated hydrocarbon by-products. The major by-products are two hexachloropentane isomers. While not wishing to be bound by any particular theory, these isomers are believed to result from combining one carbon tetrachloride molar equivalent and two vinyl chloride molar equivalents.

Additionally, partial breakdown of TBP occurs in the reaction step. While not wishing to be bound by any particular theory, the primary TBP breakdown products are believed to be 1-chlorobutane and dibutyl phosphate (DBP). DBP is believed to combine with ferric and ferrous chloride forming salts.

Reactor operating conditions are balanced between high vinyl chloride efficiency, low hexachloropentane production, high 1,1,1,3,3-pentachloropropane yield, and acceptable hexachloroethane production. Carbon tetrachloride is added in excess to vinyl chloride to suppress hexachloropentane production. The carbon tetrachloride to vinyl chloride feed ratio range is from about 1.0 moles per mole to about 3.0 moles per mole and preferably from about 1.1 moles per mole to about 2.0 moles per mole. Table 1 below tabulates the reactor operating conditions.

TABLE I

| Condition | Range | Preferred Range |
|---|---|---|
| Reactor temperature: (F.) | 175 to 250 | 210 to 235 |
| Reactor pressure: (Psig) | 10 to 100 | 25 to 40 |
| Iron/Vinyl chloride: (mol/mol) | 0.001 to 0.006 | 0.002 to 0.006 |
| TBP/VnCl: (mol/mol) | 0.001 to 0.007 | 0.002 to 0007 |
| Flash tower recycle/vinyl: (lb/lb) | 1.0 to 5.0 | 2.0 to 4.0 |

Reactor contents are continually drawn from the reaction step to the catalyst recovery step. This is referred to as the reactor effluent stream.

The reactor effluent stream is preferably drawn from a sedimentation pot, or more preferably, from a reactor's internal sedimentation tube. This device provides a still zone, separating coarse particles from reactor effluent and facilitating the return of coarse iron to the reaction mixture. The function of this device is to retard unconverted iron powder loss from the reactor. It has been found that this is an improvement due to the effects discussed below.

First the preferred chemical reaction takes place only in the presence of vinyl chloride, carbon tetrachloride, and catalyst in the reactor where all are intimately mixed. The presence of iron in the catalyst recovery step serves no useful purpose. Moreover, iron present in this recovery step will react with ferric chloride to form ferrous chloride. The ferrous chloride, however, is very reactive and is believed to produce unwanted by-products. Thus, minimizing the presence of iron powder in the catalyst recovery step minimizes the formation of by-products. Accordingly, selectivity is increased.

Second, iron particles can function as nuclei, promoting formation of deposits in the catalyst recovery equipment. These deposits can grow to the point where they interfere with the equipment operation, increasing downtime necessary to clean the equipment. Hence, use of the sedimentation pot/internal sedimentation tube can also increase on-stream time.

Third, with less iron lost to reactor effluent, the usage of iron powder is more efficient.

In another exemplary preferred embodiment, a sedimentation tube which is a simple device is provided. The manufactured tube need not be complex. Moreover, it should trap coarse iron (the majority of iron mass) in the reactor while allowing other particulate fines (i.e., impurity inclusions in iron powder) to escape. Hence, the sedimentation tube may also be referred to as a coarse particle separator.

The diameter of the sedimentation tube may be set by unhindered settling velocity. While not wishing to be bound by any particular theory, the operator may calculate settling velocity for iron particles decreased to half original diameter by reaction with ferric chloride—then install a sedimentation tube with a diameter giving the same draw velocity. Theoretically, at least 88% of the original particle mass must be digested before the particle can rise to the effluent draw point. Continued digestion further limits the number of remaining particles to be drawn into the reactor effluent stream.

Catalyst Recovery Step

The catalyst recovery step distills reactor effluent into distillate and bottoms fractions. The distillate fraction, is shown in the FIGURE of drawing as flash tower distillate containing unconverted carbon tetrachloride, unconverted vinyl chloride, 1,1,1,3,3-pentachloropropane, trace light by-products and trace heavy by-products. Examples of light by-products include 1-chlorobutane, chloroform, hexachloroethane and 1,1,2-trichloroethane. On the other hand, examples of heavy by-products include hexachloropentane isomers and hexachlorobutadiene. Substantially all carbon tetrachloride and vinyl chloride entering the catalyst recovery step leave as flash tower distillate components. The majority of the 1,1,1,3,3-pentachloropentane entering this step is recovered in flash tower distillate.

The bottom fraction contains ferric chloride, TBP, hexachloropentane isomers, 1,1,1,3,3-pentachloropropane, and high boiling point components. Substantially all catalyst components remain in the bottom fraction. The bottom fraction is continually drawn from the recovery equipment in two streams, flash tower recycle and flash tower purge. The purge stream is sent either to a secondary recovery process or to a disposal process. The recycle stream is sent to the reactor, where ferric chloride and TBP content resumes the role of catalyst components.

The catalyst recovery equipment in this description is called the flash tower. The process-wetted area of the flash tower is preferably constructed of the same materials listed for the reactor. The flash tower contains a distillation section, having an internal structure promoting liquid vapor contact. Trays and random or structured packing are exemplary of the internal structure which may be utilized to promote vapor liquid contact. The flash tower upper part is equipped with a means for condensing vapor, preferably an external condensing system. The flash tower lower part is equipped with a means for vaporizing the bottom fraction, preferably an external reboiler. As defined herein, a flasher tower lower part is any section of the flasher tower below the reactor effluent's entry point into the catalyst recovery system.

The flash tower is preferably operated under partial vacuum. Partial vacuum operation allows bottom fraction vaporization at lower temperature. Flash tower bottom temperature is controlled to prevent excessive TBP breakdown and by product formation. Flash tower residence time, defined and discussed in the following examples, influences the operating bottom temperature range. A flash tower bottom may be operated at a temperature below 240° F., but preferably below 220° F. The flash tower operating pressure ranges from about 15 to 50 TORR, but preferably from about 20 to 30 TORR. High boiling by-products dilute the catalyst components to keep the bottom fraction fluid, thus allowing recycle to the reactor with simple pumps. The flash tower recycle stream is a substantial reactor feed, providing the majority of ferric chloride and TBP entering the reaction step. As the majority of catalyst components are continually cycled through reaction and catalyst recovery steps, this is regarded as an integrated process. Further, once the process of the invention has been initiated, there is no need for refortification with fresh ferric chloride feed.

Purification Step

Two distillation towers disposed in series are utilized to separate 1,1,1,3,3-pentachloropentane from lighter and heavier compounds. One distillation tower, the light tower, is used to separate lighter components. Naturally, this tower can be disposed on the second one in the series in the process, but is preferably first. The distillate fraction of the light tower contains unconverted vinyl chloride, unconverted carbon tetrachloride, and other light by-products. A portion of the light distillate may be recycled to the reaction step, improving feedstock conversion for the overall process. This is the light recycle stream as shown in the FIGURE of the drawing. A purge stream, light purge, is drawn to control accumulation of light by-products. Examples of light by-products include chloroform, 1-chlorobutane, 1,1,2-trichloroethane, and tetrachloropropene. The first tower is operated under partial vacuum, maintaining bottom temperature to preferably less than 280° F. Higher bottom temperature leads to by-product formation.

The second distillation tower of the process is preferably the product tower. Heavy components are separated from 1,1,1,3,3-pentachloropropane in this tower. Examples of heavy components include 1,1,1,2,3-pentachloropentane (an isomer of the product), hexachlorobutadiene, and hexachloropentane isomers. This tower is operated under partial vacuum, maintaining bottom temperature to preferably less than 280° F.

The entire process is operated on a continuous basis and can be sized to produce from several pounds per day to millions of pounds per year of 1,1,1,3,3-pentachloropropane.

EXAMPLES

In order to further illustrate the production of 1,1,1,3,3-pentachloropropane the following examples are given. It will be understood that same are intended only as illustrative and in no way limiting.

Example 1

Production of 1,1,1,3,3-Pentachloropropane at a High Carbon Tetrachloride to Vinyl Chloride Feed Ratio A pilot plant was constructed as shown in the FIGURE of the drawing using a 10 gallon glass-lined reactor and a nickel flash tower. It was operated at the conditions listed in Table II below. These results illustrate that the novel production process efficiently converts the vinyl and $CCl_4$ feed materials to 1,1,1,3,3-pentachloropropane (HCC240fa) at a $CCl_4$ to vinyl molar feed ratio of 1.7. The results presented are the average of eight samples. In this table and in the following examples, the selectivity to HCC240fa is estimated as the number of moles of vinyl chloride converted to HCC240fa divided by the number of moles of vinyl chloride converted to all products. In this and the following examples, the residence time in the flasher is calculated as the liquid inventory in the flasher and reboiler [lb] divided by the rate of flash tower purge [lb/day]. The inventory in all cases herein was 75 lb.

TABLE II

| Feed ratios into reactor | | |
| --- | --- | --- |
| $CCl_4$/VnCl | Mol/mol | 1.7 |
| Fe metal/VnCl | Mol/mol | 0.0031 |
| [fresh TBP]/VnCl | Mol/mol | 0.0031 |
| [flash tower recycle]/VnCl | lb/lb | 3.4 |
| [light recycle]VnCl | lb/lb | 0.0 |
| Other Conditions | | |
| reactor residence time | Hours | 9.0 |
| reactor pressure | Psig | 33 |
| reactor temperature | ° F. | 225 |
| flasher pressure | Torr | 25 |
| flasher temperature (liquid) | ° F. | 203 |
| flasher residence time | Days | 13 |
| Results | | |
| VnCl Conversion | % | 96.5 |
| VnCl Selectivity to HCC240fa | % | 95.7 |

Example 2

Production of 1,1,1,3,3-Pentachloropropane at Low Carbon Tetrachloride to Vinyl Chloride Feed Ratio The pilot plant process described above was operated at the conditions listed in Table III below. These results illustrate that the novel production process efficiently converts the vinyl and $CCl_4$ feed materials to 1,1,1,3,3-pentachloropropane at a CCl to vinyl molar feed ratio of 1.3. The results presented are the average of eight samples.

TABLE III

| Feed ratios into reactor | | |
| --- | --- | --- |
| $CCl_4$/VnCl | Mol/mol | 1.3 |
| Fe metal/VnCl | Mol/mol | 0.0031 |
| [fresh TBP]/VnCl | Mol/mol | 0.0031 |
| [flash tower recycle]/VnCl | lb/lb | 3.2 |
| [light recycle]VnCl | lb/lb | 0.0 |

TABLE III-continued

Other Conditions

| | | |
|---|---|---|
| reactor residence time | Hours | 9.0 |
| reactor pressure | Psig | 33 |
| reactor temperature | °F. | 225 |
| flasher pressure | Torr | 25 |
| flasher temperature (liquid) | °F. | 203 |
| flasher residence time | Days | 7.5 |
| Results | | |
| VnCl Conversion | % | 94.8 |
| VnCl Selectivity to HCC240fa | % | 93.3 |

Comparative Example 3

Poor Results When Flasher is Operated Incorrectly

This example shows that incorrect operation of the flasher (the catalyst recovery step shown in the FIGURE of the drawing) can produce poor results. As shown in the FIGURE, some of the flasher liquid is purged as a waste stream in order to allow the unwanted high-boiling by-products such as 1,1,1,3,5,5-hexachloropentane (HCC-470jfdf) and 1,1,3,3,5,5-hexachloropentane (HCC-470nfaf) to exit the reactor/flasher system. The flasher liquid contains some 1,1,1,3,3-pentachloropropane (HCC240fa) product. Thus, to minimize the loss of useful HCC240fa product in this waste stream, the purge rate must be minimized. Reducing the purge rate results in an increase in the HCC470jfdf and HCC470nfaf concentrations and a decrease in the HCC240fa concentration in the flasher liquid. This, in turn, causes an increase in the temperature of the boiling liquid, at a given pressure. The residence time of the high-boiling components of the flasher liquid is on the order of several to many days.

On one occasion, the pilot plant reactor/flasher system mentioned in Example 1 was operated with the goal of improving net production of HCC240fa product overhead from the flasher, by minimizing losses to the flasher purge stream. For a period of about 7 days, the flasher was operated at a very low purge rate, which averaged about 0.13 lb per hour. The liquid inventory in the flasher system was about 75 lb. One possible measure of the mean residence time of the flasher liquid in the flasher is:

$$t = 75/0.13/24 = 24 \text{ days.}$$

The average temperature of the flasher liquid during this time period was about 232° F. The average concentration of phosphorus in the flasher liquid during this time period was 0.9 wt % and the average concentration of ferric chloride was 2.8 wt %. Toward the end of this time period, the system was showing symptoms suggesting fouling of the reboiler tubes. The system was shut down and inspected. It was found that the flasher reboiler tubes were thickly coated inside with a black solid material, which was quite difficult to remove. The solid material contained large amounts of iron and phosphorus compounds.

Comparative Example 4

Catastrophic Failure of Flash Tower Recycle Material

This example again shows that incorrect operation of the flasher can produce disastrous consequences. Aliquots from a sample of flasher bottoms liquid taken from the pilot plant flasher were placed in glass flasks fitted with a magnetic stirrer, a reflux condenser, and a nitrogen pad. The mixtures were heated and stirred at 221° F. and 203° F., respectively, under a nitrogen pad for several days. Several samples of liquid were taken during this time and analyzed via gas chromatography.

The sample aliquot that was heated at 203° F. was beginning to fail catastrophically after 11 days. The sample that was heated at 221° F. failed catastrophically after only 4 days. Catastrophic decomposition is characterized by the formation of large amounts of solids, caused by the precipitation of materials that contain iron and phosphorus compounds. The compounds 1,1,3,3-tetrachloropropene and hydrogen chloride are also generally produced during catastrophic failure, and tributylphosphate is converted to butyl chloride and various phosphorus-containing compounds.

For the aliquot that was heated at 221° F., black solids had formed and were stuck to the glass flask walls after 3.9 days. The concentration of tributylphosphate (TBP) had declined from 3.1 wt % to 2.1 wt % after 2.9 days, and finally to 0.4 wt % after 5.0 days. Dehydrochlorination of HCC-240fa had produced only 0.08 wt % 1,1,3,3-tetrachloropropene after 3.9 days, after which substantial dehydrochlorination occurred, finally producing 1.9 wt % 1,1,3,3-tetrachloropropene after five days. After five days, 90% of the initial soluble iron had precipitated as solids, but virtually none did before 3.9 days.

For the aliquot that was heated at 205° F., there were no solids visible until more than 7 days had passed. The concentration of TBP was 1.5 wt % after 11 days, and only small amounts of solids had formed at that time. The soluble iron concentration was virtually unchanged during the whole period. Dehydrochlorination to increase the rate of production of 1,1,3,3-tetrachloropropene was setting in, indicating the onset of the catastrophic decomposition process.

These tests illustrate that if flasher bottoms liquid is heated for several days catastrophic decomposition can occur, producing large amounts of solids and gas. In a commercial HCC240fa plant, flasher bottoms liquid is held in the flasher and reactor system for periods of several days to several weeks, and it is heated at temperatures comparable to these batch tests. The batch tests show that the liquid fails more quickly at higher temperatures, and that, at a given residence time, there is a maximum temperature beyond which sustained operation is very risky. If catastrophic decomposition were to occur in a commercial system, the production of solids would require that the flasher be shut down for cleaning.

Example 5

Effect of Iron Metal in the Flash Tower

Examples 5 and 6 will show that the presence of iron metal powder in the flasher increases the rate of degradation of the flasher bottoms liquids. The present example is the control test, with no iron metal added.

A sample of flasher bottoms liquid taken from the pilot plant flasher was placed in a glass flask fitted with a magnetic stirrer, a reflux condenser and a nitrogen pad. The reaction mixture was heated and stirred at 105° C. under nitrogen for a period of five days. Several samples of liquid were taken during this time and analyzed via gas chromatography. Results are shown in Table IV below. No solids were present after heating for 2.9 days. Black solids had formed and were stuck to the glass flask walls as 3.9 days had elapsed. The concentration of tributylphosphate (TBP) had declined from 3.1 wt % to 2.1 wt % after 2.9 days, and finally to 0.4 wt % after 5.0 days. Dehydrochlorination of HCC-240fa had produced only 0.02 wt % 1,1,3,3-tetrachloropropene by 2.9 days lapsed, and 0.08 wt % at 3.9 days. Substantial dehydrochlorination occurred between 3.9 and 5.0 days, finally producing 1.9 wt % 1,1,3,3-tetrachloropropene. After five days, the initial soluble iron had precipitated as solids, but virtually none did before 3.9 days.

TABLE IV

Table IV: No iron metal present

| | | Starting Material | Sample 1 | Sample 2 | Sample 3 |
|---|---|---|---|---|---|
| Elapsed Time | Days | 0.0 | 2.9 | 3.9 | 5.0 |
| Appearance of reaction mixture | | clear brown | black, solids visible | some solids visibly stuck to the walls of the flask | lots of solids present |
| 1,1,3,3-tetrachloropropene | wt % | 0.00 | 0.02 | 0.08 | 1.92 |
| TBP | wt % | 3.0 | 2.1 | 1.8 | 0.4 |
| Dissolved iron | wt % | 0.8 | 0.8 | 0.8 | 0.1 |
| Non-volatile materials | wt % | N/A | N/A | N/A | N/A |

Example 6

Effect of Iron Metal in the Flash Tower

The same flasher bottoms material tested in Example 5 was tested according to the procedure of Example 5, except that 1.1 wt % of iron metal powder was added to the reactor with the flasher bottoms. The results are shown in Table V below. In this case, significant degradation had occurred after only 1.2 days, evidenced by the formation of 0.46 wt % 1,1,3,3-tetrachloropropene. Substantial degradation had occurred by 1.9 days elapsed, as shown by the decline of TBP concentration to 0.4 wt %, the increase in 1,1,3,3-tetrachloropropene to 1.3 wt %, and the increase in non-volatile materials from the initial 13 wt % to 20 wt %. The presence of iron metal, therefore, substantially reduced the time required for serious degradation of the material to occur.

TABLE V

Table IV: No iron metal present

| | | Starting Material | Sample 1 | Sample 2 |
|---|---|---|---|---|
| Elapsed Time | Days | 0.0 | 1.2 | 1.9 |
| Appearance of reaction mixture | | clear brown | Black liquid, no solids visible except for suspended solids presumed to be iron powder | lots of black solids visible, stuck to the glass walls of the reactor |
| 1,1,3,3-tetrachloropropene | wt % | 0.00 | 0.46 | 1.3 |
| TBP | wt % | 2.6 | 1.9 | 0.4 |
| Dissolved iron | wt % | 0.8 | N/A | N/A |
| Non-volatile materials | wt % | 13 | N/A | 20 |

Example 7

Production of 1,1,1,3,3-Pentacbloropropane

The pilot plant mentioned in Example 1 was operated at the conditions listed in Table VI below. These results illustrate that the novel production process efficiently converts the vinyl and $CCl_4$ feed materials to 1,1,1,3,3-pentachloropropane (HCC240fa). The results presented are the average of three samples.

TABLE VI

| Feed ratios into reactor | | |
|---|---|---|
| $CCl_4$/VnCl | Mol/mol | 1.7 |
| Fe metal/VnCl | Mol/mol | 0.0042 |
| [fresh TBP]/VnCl | Mol/mol | 0.0047 |
| [flash tower recycle]/VnCl | lb/lb | 2.0 |
| [light recycle]VnCl | lb/lb | 0.0 |
| Other Conditions | | |
| reactor residence time | Hours | 7.8 |
| reactor pressure | Psig | 35 |
| reactor temperature | ° F. | 233 |
| flasher pressure | Torr | 20 |
| flasher temperature (liquid) | ° F. | 214 |
| flasher residence time | Days | 8.7 |
| Results | | |
| VnCl Conversion | % | 95.1 |
| VnCl Selectivity to HCC240fa | % | 95.4 |

Example 8

Sedimentation Tube Operation

Reactor effluent was drawn from a sedimentation tube at 0.00086 feet per second average velocity. The reactor was continually fed with powder iron, having particle diameter less than 44 microns for 95 percent of particles. Unhindered settling velocity for 22-micron particles was calculated for density and viscosity conditions at 0.0014 feet per second. Elemental iron concentration was calculated from the weight of iron remaining on 5-micron filter papers following sample filtration. Samples of reactor fluid indicated the average elemental iron concentration in the reactor was 56 parts per million by weight. Particle analysis for reactor effluent samples had been discontinued because previous experience showed elemental iron was non-detectable (less than 5 ppm) in reactor effluent for similar flow conditions.

While the invention has been described in terms of preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A process for the production of 1,1,1,3,3-pentachloropropane, comprising:

a) producing a product mixture in a reactor by reacting carbon tetrachloride and vinyl chloride in the presence of a catalyst mixture comprising organophosphate solvent, iron metal and ferric chloride under conditions sufficient to produce 1,1,1,3,3-pentachloropropane;

b) subjecting the 1,1,1,3,3-pentachloropropane-containing product mixture from step (a) to distillation such that a fraction enriched in 1,1,1,3,3-pentachloropropane is separated from the product mixture and a bottoms fraction results which comprises the organophosphate/ferric chloride catalyst components and heavy end by-products; and c) recycling at least a portion of the bottoms fraction from step (b) to the reactor.

2. The process according to claim 1, wherein fresh ferric chloride is not added once the process has been initiated.

3. The process according to claim 1, wherein the organophosphate solvent is tributyl phosphate.

4. The process according to claim 1, wherein the molar ratio of carbon tetrachloride to vinyl chloride in step (a) ranges from about 1.3:1 to about 2:1.

5. The process according to claim 1, wherein the fraction enriched in 1,1,1,3,3-pentachloropropane is subjected to a distillation so as to remove light-end boiling components.

6. The process according to claim 1, wherein the fraction enriched in 1,1,1,3,3-pentachloropropane is subjected to a further distillation such that 1,1,1,3,3-pentachloropropane is boiled off and higher boiling components remain in the distillation vessel.

7. The process of claim 1, wherein step (b) is operated at a liquid temperature of up to 240° F., and such that the ratio of the liquid inventory [lbs] to the rate of flash tower purge [lb/day] is less than about 24 days.

8. The process of claim 1, wherein a sedimentation device is employed to separate coarse particles from the reactor effluent, and thereby prevent large particles of iron from entering the flash tower used in step (b).

* * * * *